United States Patent [19]

Colle et al.

[11] Patent Number: 4,725,614

[45] Date of Patent: Feb. 16, 1988

[54] AZOLYL DERIVATIVES OF CARBOCYCLIC AND HETEROCYCLIC KETONES HAVING FUNGICIDAL ACTIVITY

[75] Inventors: Roberto Colle, Basiglio; Giovanni Camaggi, Lodi; Franco Gozzo, San Donato Milanese; Luigi Mirenna, Milan, all of Italy

[73] Assignee: Montedison S.p.A., Milan, Italy

[21] Appl. No.: 802,001

[22] Filed: Dec. 3, 1985

[30] Foreign Application Priority Data

May 14, 1984 [IT] Italy ............................ 20919 A/84
May 14, 1985 [WO] PCT Int'.Appl. . PCT/EP85/00229

[51] Int. Cl.$^4$ ................. A01N 43/653; C07D 249/08; C07D 405/06
[52] U.S. Cl. .................. 514/383; 548/262; 548/341; 514/399
[58] Field of Search ............... 548/262; 514/383, 688

[56] References Cited

U.S. PATENT DOCUMENTS

| | | | |
|---|---|---|---|
| 4,472,415 | 9/1984 | Worthington et al. | 548/262 |
| 4,582,843 | 4/1986 | Timmler et al. | 548/262 |
| 4,636,247 | 1/1987 | Clough et al. | 548/262 |
| 4,670,041 | 6/1987 | Payne et al. | 548/262 |
| 4,670,454 | 6/1987 | Janssen et al. | 548/262 |

FOREIGN PATENT DOCUMENTS 2831235  1/1980  Fed. Rep. of Germany ...... 548/262

*Primary Examiner*—Glennon H. Hollrah
*Assistant Examiner*—Patricia L. Morris
*Attorney, Agent, or Firm*—Stevens, Davis, Miller, and Mosher

[57] ABSTRACT

There are disclosed compounds having general formula (I):

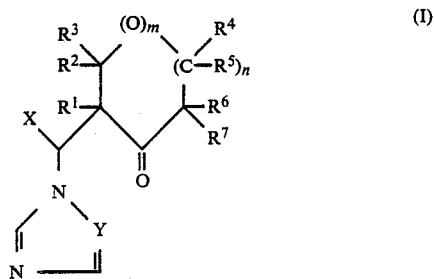

wherein: X is H, a phenyl, phenylalkyl, phenylcarbonyl, phenyloxy group, optionally substituted with a halogen; Y is N or CH; $R^1$ is H or a phenyl group; $R^2$ and $R^3$, equal or different, are H, an alkyl, alkoxy group or together they are an atom of ketonic oxygen; $R^4$ and $R^5$, equal or different, are H or an alkyl group; $R^6$ and $R^7$, equal or different, are H, an alkyl group or one of them forms with $R^2$ or $R^3$ an alkylidenic or etheric bridge; or they form a dioxyalkylidenic or alkylidenic ring; m=0, 1; n=0, 1, 2, 3. The compounds are endowed with fungicide and systemic properties.

5 Claims, No Drawings

AZOLYL DERIVATIVES OF CARBOCYCLIC AND HETEROCYCLIC KETONES HAVING FUNGICIDAL ACTIVITY

The present invention relates to new azolyl derivatives of carbocyclic or heterocyclic ketones having a high fungicide activity, to the preparation of said compounds and to the use of same in agriculture.

More particulary, the new class of compounds, object of the present invention is represented by the following general formula I:

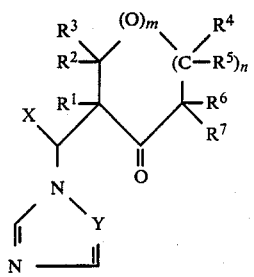

wherein:
x represents a H atom, a phenyl group optionally substituted by one or two halogen atoms, a phenylaklyl group optionally substituted by one or two halogen atoms in the phenylic part, a phenylcarbonyl group optionally substituted by one or two halogen atoms in the phenylic part, a phenyloxy group optionally substituted by one or two halogen atoms;

Y represents a N atom or a CH group;

$R^1$ represents a H atom or a phenyl group optionally substituted by one or two halogen atoms;

$R^2$ and $R^3$, equal to or different from each other, represent a H atom, a $C_1$–$C_4$ alkyl group, a $C_1$–$C_4$ alkoxyl group, or together they represent an atom of ketonic O, or one of them forms an alkylidenic or etheric bridge with $R^6$ or $R^7$ as well;

$R^4$ and $R^5$, equal to or different from each other, represent a H atom or a $C_1$–$C_4$ alkyl group;

$R^6$ and $R^7$, equal to or different from each other, represent a H atom, a $C_1$–$C_4$ aklyl group or one of them forms an alkylidenic or etheric bridge with $R_2$ or $R_3$, or they form a dioxyalkylidenic or aklylidenic ring;

m represents a whole number: 0 or 1;

n represents a whole number: 0, 1, 2 or 3.

As it appears from general formula (I) the compounds of the present invention consist of carbocyclic or heterocyclic ketones which are linked in position 2 with respect to the ketonic group, through a methylenic or methynic bridge, to an azolyl group, said azolyl group being 1-triazolyl or 1-imidazolyl. When the connection between ketone and azolyl ring takes place through a methynic bridge, this latter is further more linked to an aryl, an aralkyl, an aryloxy or an arylcarbonyl group, where with aryl group a phenyl groupis meant, that is optionally substituted in the ortho and para positions by one or two halogen atoms, preferably Cl and F. The compounds of formula (I) are endowed with a high fungicidal activity and with other useful properites, hereinafter described, which allow to make sure of such compounds in agriculture for protecting useful plants from the action of the phytopathogenous fungi.

Therefore a further object of the present invention consists in the use of the compounds of formula (I) as fungicides in agriculture and the fungicidal compositions containing said compounds as active constituent.

A preferred group of compounds of formula (I) is the group wherein:

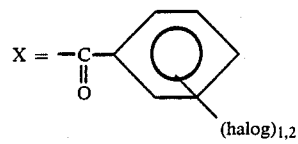

$Y = N$
$R^1 = H$

Representative examples of compounds falling under formula (I) are the following ones (the symbol TR represents 1,2,4-triazolyl-1 radical).

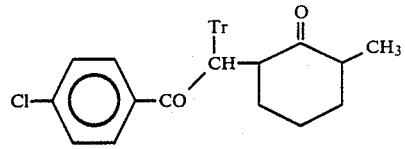

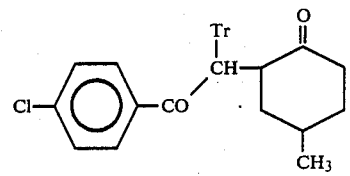

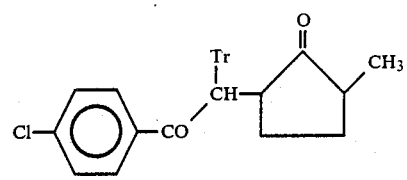

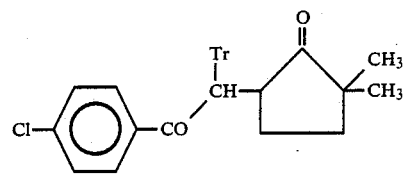

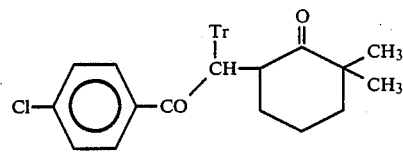

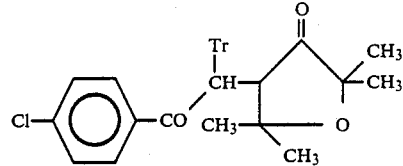

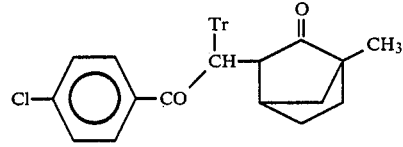

-continued
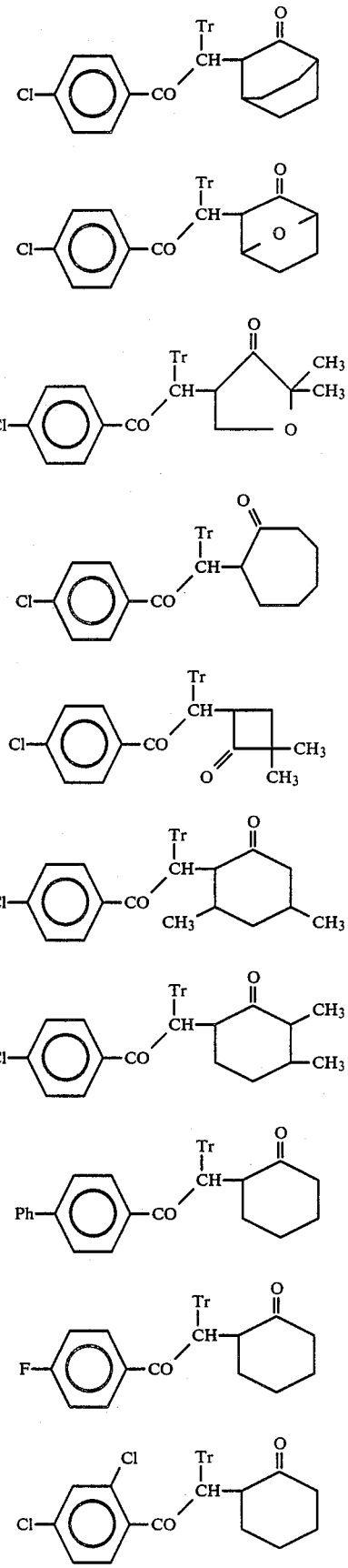
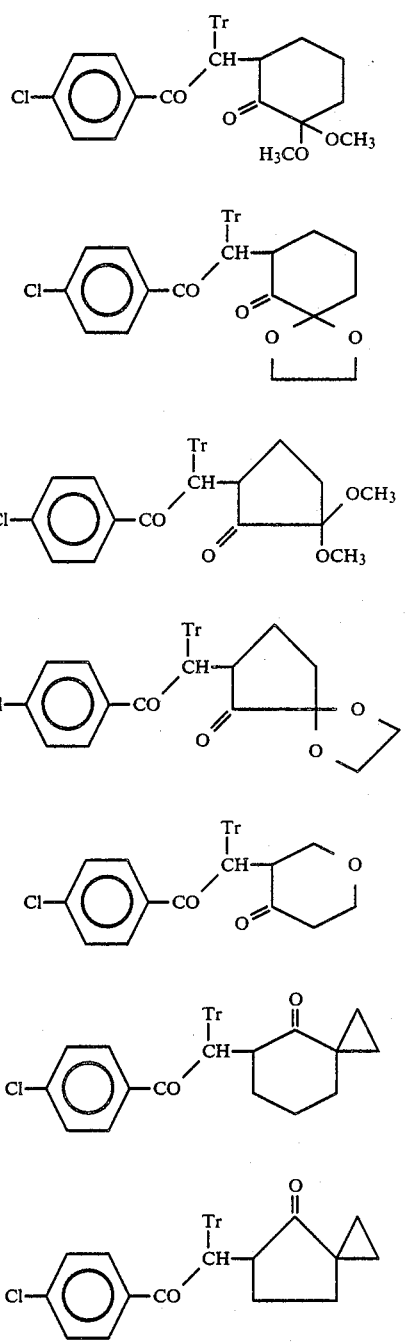
The compounds of formula (I) are prepared by making use of any one of the processes described hereinafter, where the same symbols have been employed as indicated for formula (I).
A first synthesis process to be utilized when X=H consists in condensing the azole with the suitable 2-(chloromethyl)-cycloketone according to reaction 1:

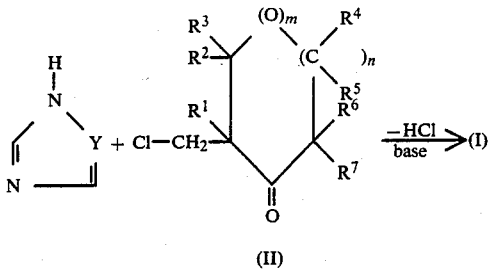

(II)

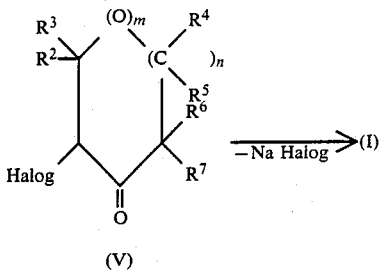

(V)

Reaction (1) is carried out in an inert solvent in the presence of a stoichiometric amount of an organic or inorganic base at temperatures ranging from 20° C. to boiling temperature of the reaction mixture.

The 2-(chloromethyl)-ketones of formula (II) are prepared, in their turn, by chloromethylation of known cycloketones according to the method for 2-(chloromethyl)-cyclohexanone described by Décombe in "Comptes Rendu Hebdomaires des Séances de l'Académie de Sciences, 213 (1941), 579".

A second synthesis process valid for $R^1 = H$ and $X = a$ mono or dihalogenated phenyl, mono or dihalogenated phenylcarbonyl, consists in condensing the azole with the suitable benzylidene or phenacylidene-cycloketone according to reaction 2:

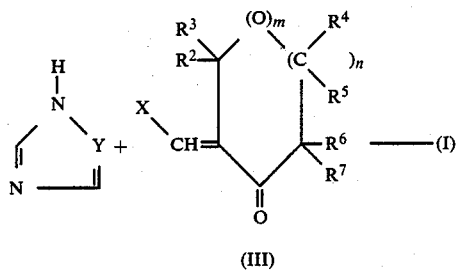

(III)

Reaction (2) is carried out in an inert solvent such as an aromatic hydrocarbon, for instance toluene, in the presence of a catalytic amount of an organic base, for instance a tertiary amine.

Alternatively reaction (2) may be carried out in a polar solvent such as dimethylformamide or ethanol in the presence of an inorganic base such as an alkali carbonate or hydroxide, in particular potassium hydroxide.

The compounds of formula (III) are prepared, in their turn, by a method, that is analogous to the one for 2-benzylidenecyclohexanone described by Vorländer, Kunze, B. 59, 2081. A third synthesis process, valid for $R^1 = H$ and $X = a$ mono or dihalogenated phenylcarbonyl consists in reacting the suitable table α-azolyl-ketone in the form of a sodium salt with a α-halocycloketone according to reaction 3:

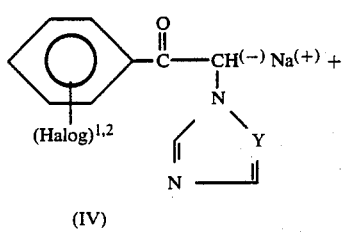

(IV)

The compounds of formula (V) can be prepared according to methods well known in literature, by halogenation of the suitable cycloketones.

As already mentioned the compounds of general formula (I) are endowed with a particularly high fungicidal activity against phytopathogenous fungi, in particular the ones included in the orders of the Ascomycetes and Basidiomycetes, infecting the growing of cerals, cucurbitaceae, vine and fruit trees. Examples of plant diseases which can be fought by means of the compounds of the present invention are the following ones:

Erysiphe graminis on cereals,

Spherotheca fuliginea on cucurbitaceae (for instance cucumber),

Puccinia on cereals,

Helminthosporium on cereals,

Podosphaera leucotricha on apple-trees,

Uncinula necator on vines,

Venturia inequalis on apple-trees,

Botrytis cinerea on tomatoes, vines, strawberries, and still other diseases.

Furthermore the compounds of formula (I) possess other positive characteristics, such as a fungicidal action having both preventive and curative character, a fungicidal action having a systemic character coming from the property of the compounds in question of penetrating into the vascular systems of the plant and of acting, through translation, in places, for instance leaves, that are very far away from the ones, they have been applied in, for instance roots.

On account of the high fungicidal activity coupled to the above mentioned positive characteristics, the fungicidal compounds of the present invention can be used for protecting a great deal of useful plants from the fungus action; among these plants we can cite: cereal (wheat, barley), cucurbitaceae (cucumber, vegetable marrow), fruit trees (apple-trees, citrus fruit), strawberries, tomato, vine.

For practical uses in agriculture it is often useful to have available fungicidal compositions containing one or more compounds of formula (I) as active ingredient.

The application of these compositions can take place on every part of the plant for instance: leaves, stalks, branches and roots, or on the seed themselves before sowing, or on the soil adjoining the plant as well. Compositions can be used, which are in form of dry powers, wettable powers, emulsifiable concentrates, pastes, granulates, solutions, suspensions etc.: the choice of the composition kind will depend on the specific use. The compositions are prepared according to the known way, for instance, by diluting or dissolving the active substance by means of a solvent medium and/or a solid diluent, optionally in the presence of surfactants. As solid diluents or carriers, use may be made of: silica, kaolin, bentonite, talc, diatomite, dolomite, calcium carbonate, magnesia, gypsum, clays, synthetic silicates, attapulgite, sepiolite. As liquid diluents, besides, of course, water, use may be made of various kinds of solvents, for instance aromatic solvents (benzol, xylols, or mixtures of alkylbenzols), chloroaromatic solvents (chlorobenzol), parafins (oil fractions), alcohols (methanol, propanol, butanol), amines, amides (dimethylformamide), ketones (cyclohexanone, acetophenone, isophorone, ethylamylketone), esters (isobutyl acetate). As surfactants: sodium salts, calcium salts, triethanolamine of aklysulfates, alkylsulfontaes, alkylarylsulfonates, polyethoxylated alkylphenols, fatty alcohols condensed with ethylene oxide, polyethoxylated fatty acids, polyethoxylated sorbitol esters, polyethoxylated fats, ligninsulfonates. The compositions may also contain special additives for particular purposes, for instance adhesion agents such as gum-arabic, polyvinyl alcohol, polyvinylpyrrolidone. If desired, it is possible to add to the compositions object of the present invention other compatible active substances as well, such as fungicides, phytodrugs, phytogrowth regulators, herbicides, insecticides, fertilizers.

The concentration of active substance in the aforesaid compositions can vary within a wide range, depending on the active compound, the cultivation, the pathogen, environmental conditios and the kind of formulation that has been used.

Generally the concentration ranges from 0.1 to 95, preferably from 0.5 to 90% by weight.

The following examples will illustrate the invention

EXAMPLE 1

Preparation of compound 1-(4-chlorophenyl)-2-(2-oxo-1-cyclohexyl)-2-(1-triazolyl)-ethanone. Compound No. 1.

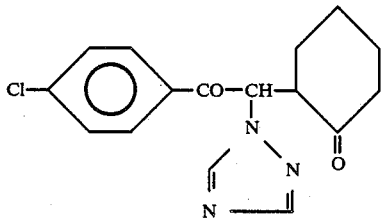

5 g (0.0266 moles) of 1-(4-chlorophenyl)-2-(1-triazolyl)-ethanone—in 20 ml of anhydrous DMF were added, drop by drop and under a nitrogen atmosphere, to a suspension at 20° C. of 1.08 g of sodium hydride in oil at 505% (0.0226 moles) in 20 ml of DMF.

The mixture was kept under stirring for at least 30 minutes at room temperature. At the end of this period of time the limpid, dark-red colored solution of the sodium salt of triazolylketone, was added slowly, always under nitrogen atmosphere, to a solution of 3 g of 2-chlorocyclohexanone (0.0226 moles) in 20 ml of anhydrous DMF, keeping the temperature between 5 and 10° C.

After 8 hours under stirring at room temperature, the reaction mixture was poured into 500 ml of $H_2O$. The separated oil was extracted by means of ether and after solvent evaporation the product was purified on chromoatographic column. 3 g of purified 1-(4-chlorophenyl)-2-(-2-oxo-cyclohexyl)-2-(1-triaxoyl)-ethanone were obtained as a vitreous solid.

$^1H$ NMR: 8,2 (s, 1H), 8 (s, 1H), 7,9-7,4 (m,4H), 6,15 (d,1H), 0, 3,6 (d,t, 1H), 2,9-1,3 (m, 8H).

IR: 1700, 1590, 1505, 1490, 1280 $cm^{-1}$.

EXAMPLE 2

Determination of the Fungicidal Activity Against Cucumber Oidium [*Sphaerotheca Fuligenea* (Schlech) Salmon].

Preventive acitivy:

Cucumber plants c.v. Marketer, grown in pot in a conditioned environment, were sprayed on the lower leaf face with the products under examination in a water-acetone solution containing 20% of acetone (vol/vol.) Then the plants were kept in a conditioned environment for 6 days and at the seventh day they were sprayed on the upper leaf face with an aqueous suspension of conidia of *Sphaerotheca fuliginea* (200.00 conidia per ml). The plants were then carried back into a conditioned environment.

At the end of the incubation period of the fungus (8 days), the infection degree was evaluated by means of indexes of a valuation scale ranging from 100 (=sound plant) to 0 (=completely infected plant).

Curative activity:

Cucumber plants c.v. Marketer, grown in pot in a conditioned environment, were sprayed on the upper leaf face with an aqueous suspension of conidia of *Sphaerotheca fuliginea* (200.00 conidia ml). After 24 hours from the infection the plants were treated with the products under examination in a water-acetone solution containing 20% of acetone (vol/vol.), by spraying both leaf faces.

At the end of the incubation period of the fungus (8 days), during which time the plants were kept in a suitably conditioned environment, the infection degree was evaluated by means of indexes of a valuation scale ranging from 100 (=sound plant) to 0 (=completely infected plant).

Systemic preventive activity by treatment through radical way:

Cucumber plants c.v. Marketer, grown in pot in a conditioned environment were treated by addition to the soil of an aqueous dispersion of the product under examination.

After 24 hours the leaves were sprayed on the upper face, with an aqueous suspension of *Sphaerotheca fuliginea* (200.000 conidia per ml).

At the end of the incubation period of the fungus (8 days) the infection degree was evaluated at sight by means of indexes of a valuation scale ranging from 100 (=sound plant) to 0 (completely infected plant). The results of these tests were set forth in Table 1.

TABLE 1

| FUNGICIDE ACTIVITY AGAINST CUCUMBER OIDIUM | | | |
|---|---|---|---|
| Compound No | Dose (g/l) | Preventive Activity | Curative Activity | Systemic radical activity |
| 1 | 0.5 | 100 | 100 | 100 |
|   | 0.25 | 100 | 100 | 100 |
|   | 0.125 | 100 | 100 | 100 |
|   | 0.06 | 100 | 100 | 100 |

EXAMPLE 3

Determination of the Fungicidal Activity Against Wheat Oidium (*Eerysiphe Graminis D. C.*)

Curative activity:

The leaves of wheat c.v. Irnerio, grown in pot in a conditioned environment, were sprayed on both leaf faces with an aqueous suspension of *Erysiphe Graminis* (200.00 conidia per cc.). After; a stay time of 24 hours in a room saturated with moisture, at 21° C., the leaves were treated with the products under examination in a water-acetone solution containing 20% of acetone (vol/vol) by spraying both leaf faces.

At the end of the incubation period (12 days), the infection degree wav evaluated at sight, by means of indexes of a valuation scale ranging from 100 (=sound plant) to 0 (=completely infected plant).

The results are set forth in Table 2.

TABLE 2

| FUNGICIDE ACTIVITY AGAINST WHEAT OIDIUM | | |
|---|---|---|
| Compound | Dose (9/1) | Curative Activity |
| 1 | 0.5 | 100 |
|  | 0.25 | 100 |
|  | 0.125 | 100 |
|  | 0.06 | 100 |

We claim:

1. Compounds of general formula:

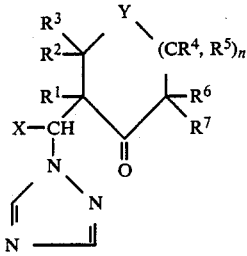

wherein:
X represents a phenylcarbonyl group, optionally substituted by one or two halogen atoms in the phenylic part, a phenyloxy group optionally substituted by one or two halogen atoms;
Y represents an oxygen atom or a $CH_2$ group;
$R^1$ represents a H atom or a phenyl group optionally substituted by one or two halogen atoms;
$R^2$ and $R^3$, equal to or different from each other, represent a H atom, a $C_1-C_4$ alkyl group, a $C_1-C_4$ alkoxyl group, or together they represent an atom of ketonic O;
$R^4$ and $R^5$, equal to or different from each other, represent a H atom or a $C_1-C_4$ alkyl group;
$R^6$ and $R^7$, equal to or different from each other represent a H atom, a $C_1-C_4$ alkyl group;
n means 0, 1, 2 or 3.

2. Compounds according to claim 1, wherein:
X represents a phenylcarbonyl group substituted by one or two halogen atoms, preferably Cl and F;
Y represents a N atom;
$R^1$ represents a H atom.

3. The compound having formula:

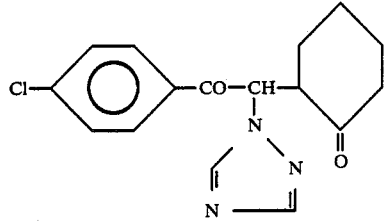

4. A method for fighting fungus infections in useful plants consisting in distributing on the plants or in the area where they grow, when the fungus infection is foreseen or it is already in progress, an effective amount of a compound according to claim 1, as such or in the form of a suitable composition.

5. A fungicidal composition comprising an effective amount having as active ingredient one or more compounds according to claim 1, together with an inert solid or liquid carrier.

* * * * *